United States Patent [19]

Anapliotis et al.

[11] Patent Number: 4,963,154
[45] Date of Patent: Oct. 16, 1990

[54] ACETABULAR CUP AS PART OF A HIP JOINT PROSTHESIS

[75] Inventors: Emanuel Anapliotis; Curt Kranz; Wiebke Ploetz, all of Berlin, Fed. Rep. of Germany

[73] Assignee: Mecron medizinische Produkte GmbH, Berlin, Fed. Rep. of Germany

[21] Appl. No.: 362,146

[22] Filed: Jun. 6, 1989

[30] Foreign Application Priority Data

Jun. 6, 1988 [DE] Fed. Rep. of Germany ... 8807481[U]
Aug. 26, 1988 [DE] Fed. Rep. of Germany ... 8810783[U]

[51] Int. Cl.$^5$ ............................................. A61F 2/32
[52] U.S. Cl. .................................... 623/22; 623/18
[58] Field of Search ................................. 623/22

[56] References Cited

U.S. PATENT DOCUMENTS

| | | | |
|---|---|---|---|
| 3,723,995 | 4/1973 | Baumann | 623/22 |
| 3,875,593 | 4/1975 | Shersher | 623/22 |
| 4,164,794 | 8/1979 | Spector et al. | 623/22 |
| 4,770,661 | 9/1988 | Oh | 623/22 |
| 4,795,469 | 1/1989 | Oh | 623/22 |

FOREIGN PATENT DOCUMENTS

| | | | |
|---|---|---|---|
| 0065482 | 11/1982 | European Pat. Off. | |
| 2839661 | 9/1979 | Fed. Rep. of Germany | |
| 3147707 | 12/1982 | Fed. Rep. of Germany | |
| 8429350 | 1/1985 | Fed. Rep. of Germany | |
| 2138304 | 10/1984 | United Kingdom | 623/22 |

Primary Examiner—Randall L. Green
Assistant Examiner—Stephanie L. Iantorno
Attorney, Agent, or Firm—Spencer & Frank

[57] ABSTRACT

Acetrabular cup as part of a hip joint prosthesis is composed of an outer support ring and a plastic inner socket insertable into the support ring. The acetabular cup includes a covering cap provided with at least one metal surface which covers the part of the inner socket not surrounded by the support ring and whose metal outer contour supplements the socket to give it the spherical shape of an essentially closed hemisphere or spherical cap.

10 Claims, 1 Drawing Sheet

ACETABULAR CUP AS PART OF A HIP JOINT PROSTHESIS

CROSS REFERENCE TO RELATED APPLICATION

This application claims the priorities of Application Ser. No. G 88 07 481.1, filed June 6, 1988 and Application Ser. No. G 88 10 783.3, filed Aug. 26, 1988, in the Federal Republic of Germany, the subject matter of which is incorporated herein by reference.

BACKGROUND OF THE INVENTION

The present invention relates to aceptabular cup of the type used with hip joint prostheses.

Such an acetabular cup having a support ring is disclosed in EP-A2-0,065,482. These prosthesis components are screwed without prior cutting into the acetabulum socket by means of a screwing tool and there have a firm seat which is sufficient for early mobility of the patient. A plastic socket can be snapped into the interior of the support ring so as to serve as a bearing for the joint ball.

The prior art support ring is screwed into the outer cortex layer of the acetabulum.

The prior art socket equipped with a self-tapping support ring is provided with a polyethylene inner socket whose cap is supported in the acetabulum through the upper ring opening. The ring structure of the support ring makes it possible for the latter to adapt itself by appropriate deformation to local conditions in the acetabulum so that threaded engagement and the introduction of forces is physiologically possible without excess local stresses on the bone structure. In this way, any bone catabolism, in particular, is avoided as it otherwise occurs in the region of local force peaks.

On the other hand, artificial hip sockets are known which are closed metal hemispheres. These sockets have the drawback that, due to their greater stiffness, they are unable to adapt themselves to the acetabulum when they are being screwed in.

SUMMARY OF THE INVENTION

It is now the object of the present invention to provide a screw-in socket of the above-mentioned type which, on the one hand, has a closed metal structure but, on the other hand, has the advantages of the prior art support ring structure.

This is accomplished by an acetabular cup.

The invention is based on the realization that the elastic separation of the regions of the socket provided with threaded sides and engaging into the bone from those regions at the vertex of the socket which are supported by the interior of the acetabulum permit optimum fixation. While the annular support structure can also be deformed during screwing in from its circular shape to an approximately elliptical shape, the basic shape of the spherical covering cap can be retained. In particular, the additional metal cap does not undesirably stiffen the socket.

The supporting function taken over by the cap region of the socket is augmented in that the vertex region is "porocoated", with the resulting porosity causing the covering cap to grow into the bone surface, thus further increasing the strength of the prosthesis seat. The ingrowth of the cap connected with the inner socket reduces the forces that, in the implanted state, must be introduced into the bone by way of the support ring.

The support ring according to the invention has the further advantage that those parts of the supporting flanks which are separated from one another only by a narrow recess (flute), as a unit, perform a supporting function since the spongy tissue remaining between the threaded portions is able to act as a "bridge" between these supporting flank components and to absorb the corresponding forces.

Advantageous modifications of the invention are defined in the dependent claims and will be described in greater detail below together with a description of the preferred embodiment of the invention with reference to the drawing figures.

DETAILED DESCRIPTION OF THE PREFERRED EMBODIMENT

Figure 1:
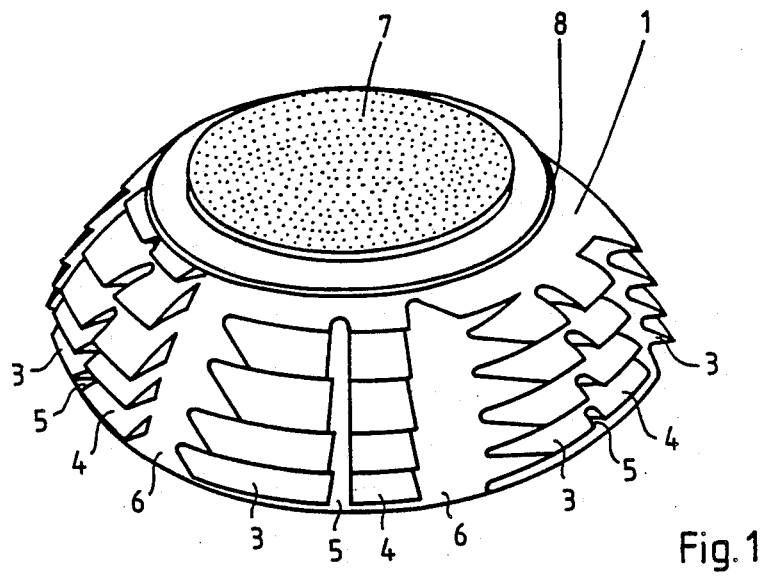
FIG. 1 is a perspective view of one embodiment of the support ring according to the invention.

The support ring 1 shown in FIG. 1 is made of titanium and serves to accommodate a plastic joint socket 2 which forms the joint bearing. A circumferential, step-shaped projection 2' provided on the inner wall serves as an abutment to support the socket.

The outer wall of the support ring is spherical (with reference to the base of the threads) so that it can be screwed in different directions into a likewise spherically milled out acetabulum without requiring further preparations, such as the cutting of threads.

Groups of supporting flanks 3 and 4 of a self-tapping thread are interrupted by flutes 5 and 6 which, on the one hand, receive the chips during the self-tapping screw-in process and, on the other hand, permit secondary fixation of the socket due to the bone chips collected there growing in.

In the illustration of FIG. 1, cap 7 is shown placed onto support ring 1. It can be seen that a gap 8 of approximately 0.5 mm in width is present between cap and support ring. This gap practically forms an "expansion groove" which compensates for deformations of support ring 1 when it is screwed into the acetabulum.

The outwardly oriented surface of the cap is provided with a porous layer (porocoat). This layer is pure titanium that is sintered on in an isostatic heat process under high pressure. The thus formed porous surface layer enhances the growth of the outer surface of cap 7 into the adjacent bone region and thus supports secondary fixation. In other words, the outer face of the covering cap 7 is porocoated. Furthermore, there can be an edge region of the outer face of cap 7 which is not porocoated.

Figure 2:
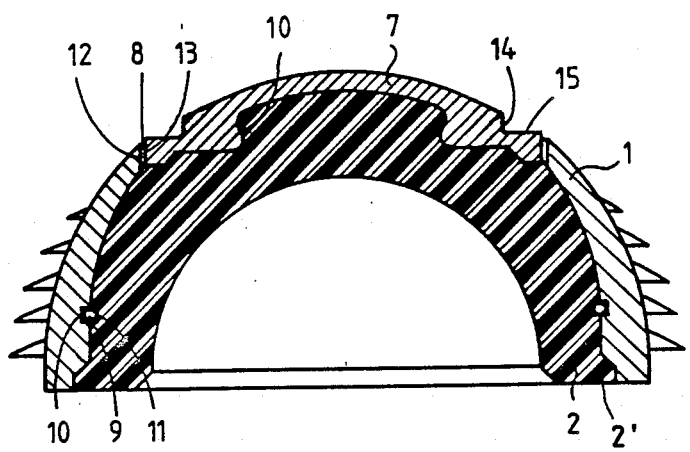
FIG. 2 is a sectional view of the embodiment of the support ring of FIG. 1.

FIG. 2 is a sectional view of the assembled socket. A polyethylene inner socket is inserted into support ring 1 which is likewise made of titanium, with the mutual fastening being effected by a metal ring 9 extending in grooves 10 and 11 of the support ring and of the inner socket, respectively. This type of connection is known and corresponds to the conventional configuration of a hip socket composed of an outer metal support ring and an inner polyethylene socket.

At the vertex of the inner socket 2, the cross section of cap 7 is cut out, with the outer surfaces of ring 1 and cap 7 supplementing one another to form a spherical outline.

In this way it is ensured that the assembled socket can be screwed in different spatial directions into an acetabulum that has been milled out in a hemispherical shape without oriented milling and prior cutting of threads being necessary.

The inner socket and cap 7 are provided with a snap connection which corresponds to that of a snap button. The inner socket is here provided with a concave projection 10 which engages in a corresponding concave recess. After the snapping, fixation occurs—corresponding to the snap button principle—by way of undercuts.

In the region of gap 8, the upper opening of support ring 1 and cap 7 are adjacent one another in the region of gap 8 with a spacing of about 0.5 mm in the region of two cylindrical faces 12 and 13, respectively, which form exterior cylinder faces and are aligned concentrically. In this way, tolerances between support ring 1 and cap 7 are compensated even during the introduction of forces as they occur in the implanted state.

By way of an annular step 14, a likewise annular edge region 15 of cap 7 lies adjacent to the central region provided with a porocoat layer. Thus, this central region is limited to that part of the socket where the forces are introduced essentially parallel to the center axis. In the implanted state, the edge formed by step 14 provides an automatic support for the cap on the adjacent bone region so that to this extent the connection between socket insert 2 and cap 7 is subjected to only slight stress.

The present invention is not limited in its embodiments to the above-described preferred embodiment. Rather, a number of variations are conceivable which take advantage of the described solution even for basically different configurations.

It will be understood that the above description of the present invention is susceptible to various modifications, changes and adaptations, and the same are intended to be comprehended within the meaning and range of equivalents of the appended claims.

What is claimed is:

1. An acetabular cup for implanting in an acetabulum, comprising:
    a metal outer support ring having inner and outer surfaces, said outer surface defining part of a hemisphere, means on said outer surface defining threads for screwing said acetabular cup into an acetabulum, and means on said inner surface defining an opening;
    a plastic inner socket having an inner and outer surface, said inner socket being received in said opening of said outer support ring, said outer surface of said inner socket being divided into first and second parts, only said first part of said outer surface of said inner socket being directly adjacent to and covered by said outer support ring, means on said inner socket defining an opening for receiving a joint ball of a hip joint prothesis therein; and
    a covering cap adjacent said outer support ring and said inner socket, said covering cap having a metal surface and covering said second part of said outer surface of said inner socket, and said covering cap further defining the hemisphere defined in part by said outer surface of said outer support ring for thereby defining a substantially complete hemisphere.

2. Acetabular cup as defined in claim 11, further comprising mechanical means for connecting said covering cap to said inner socket, and wherein the covering cap is connected with the inner socket exclusively by said mechanical means.

3. Acetabular cup as defined in claim 2, wherein said mechanical means comprises a snap-on device disposed between covering cap and said inner socket for causing the covering cap to be snapped onto the inner socket.

4. Acetabular cup as defined in claim 3, wherein the snap-on device corresponds to the shape of a snap button.

5. Acetabular cup as defined in claim 11, wherein an annular space exists between the covering cap and the support ring when the acetabular cup is assembled.

6. Acetabular cup as defined in claim 5, wherein the covering cap has a cylindrical outer wall which, when the acetabular cup is assembled, extends parallel to a corresponding inner wall of the support ring.

7. Acetabular cup as defined in claim 11, wherein the cap is made of titanium.

8. Acetabular cup as defined in claim 11, further comprising a porous coating on an outer face of the covering cap.

9. Acetabular cup as defined in claim 8, further comprising a peripheral edge on said covering cap adjacent to and surrounding said outer face, said peripheral edge having no porous coating thereon.

10. Acetabular cup as defined in claim 9, further comprising means on said peripheral edge for defining a concentric step having a substantially cylindrical, outwardly oriented, smooth wall region.

* * * * *

UNITED STATES PATENT AND TRADEMARK OFFICE
CERTIFICATE OF CORRECTION

PATENT NO. : 4,963,154
DATED : October 16, 1990
INVENTOR(S) : Emmanuel Anapliotis et al It is certified that error appears in the above-identified patent and that said Letters Patent is hereby corrected as shown below:

On the Title page, item [75]:
the first inventor's first name should read --Emmanuel--.
Claim 2, column 4, line 20, "claim 11" should read --claim 1--.
Claim 3, column 4, line 27, before "covering" and after "between" insert --said--.
Claim 5, column 4, line 32, "claim 11" should read --claim 1--.
Claim 7, column 4, line 39, "claim 11" should read --claim 1--.
Claim 8, column 4, line 41, "claim 11" should read --claim 1--.

Signed and Sealed this

Twenty-first Day of September, 1993

*Attest:*

BRUCE LEHMAN

*Attesting Officer*   *Commissioner of Patents and Trademarks*